US012678473B2

(12) United States Patent
Miura et al.

(10) Patent No.: US 12,678,473 B2
(45) Date of Patent: Jul. 14, 2026

(54) MUSCLE QUALITY IMPROVEMENT AGENT

(71) Applicant: AJINOMOTO CO., INC., Tokyo (JP)

(72) Inventors: Kyoko Miura, Kawasaki (JP); Yoshiro Kitahara, Kawasaki (JP); Haruka Ohashi, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 1055 days.

(21) Appl. No.: 17/726,731

(22) Filed: Apr. 22, 2022

(65) Prior Publication Data

US 2022/0249592 A1 Aug. 11, 2022

Related U.S. Application Data

(63) Continuation of application No. PCT/JP2020/039904, filed on Oct. 23, 2020.

(30) Foreign Application Priority Data

Oct. 25, 2019 (JP) ................................. 2019-194725

(51) Int. Cl.
| | |
|---|---|
| *A61K 38/05* | (2006.01) |
| *A23L 33/00* | (2016.01) |
| *A23L 33/18* | (2016.01) |
| *A61K 9/00* | (2006.01) |
| *A61K 38/06* | (2006.01) |
| *A61P 21/00* | (2006.01) |
| *A61P 21/06* | (2006.01) |
| *C07K 5/02* | (2006.01) |

(52) U.S. Cl.
CPC .............. *A61K 38/05* (2013.01); *A23L 33/18* (2016.08); *A23L 33/40* (2016.08); *A61K 9/0056* (2013.01); *A61K 38/06* (2013.01); *A61P 21/00* (2018.01); *A61P 21/06* (2018.01); *C07K 5/0215* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 2008/0305151 A1 | 12/2008 | Sakai et al. | |
| 2009/0136993 A1 | 5/2009 | Bridge et al. | |
| 2012/0195873 A1* | 8/2012 | Miller .................. | A61K 31/195 424/94.4 |
| 2013/0225486 A1 | 8/2013 | Breuille et al. | |
| 2013/0281394 A1* | 10/2013 | Baron ........................ | A61P 3/10 514/34 |
| 2018/0325956 A1 | 11/2018 | Breuille et al. | |

FOREIGN PATENT DOCUMENTS

| | | |
|---|---|---|
| JP | 2008-533994 A | 8/2008 |
| JP | 2014-504261 A | 2/2014 |
| JP | 2018-534273 A | 11/2018 |
| WO | WO 2007/034807 A1 | 3/2007 |
| WO | WO 2018/221526 A1 | 12/2018 |

OTHER PUBLICATIONS

Hwang et al. Eight weeks of resistance training in conjunction with glutathione and L-Citrulline supplementation increases lean mass and has no adverse effects on blood clinical safety markers in resistance-trained males. Journal of the International Society of Sports Nutrition (2018) 15:30 (Year: 2018).*
Glutathione. PubChem CID 124886. Dowloaded from https://pubchem.ncbi.nlm.nih.gov/compound/Glutathione on Jun. 30, 2025 (Year: 2025).*
Lands et al. Effect of supplementation with a cysteine donor on muscular performance. Journal of Applied Physiology, 87 (1999), pp. 1381-1385 (Year: 1999).*
Karelis et al. Effect Training Resistance With Combination In Supplementation Elderly Frail-Non In Mass Body Lean And Strength Muscle On Study (Year: 2015).*
Fragala et al. Resistance Training for Older Adults: Position Statement From the National Strength and Conditioning Association. Journal of Strength and Conditioning Research 33(8):p. 2019-2052, Aug. 2019. (Year: 2019).*
Sulmont-Rosse et al. Evidence for Different Patterns of Chemosensory Alterations in the Elderly Population: Impact of Age Versus Dependency, Chemical Senses, vol. 40, Issue 3, Mar. 2015, pp. 153-164 (Year: 2015).*
International Search Report issued Dec. 22, 2020 in PCT/JP2020/039904 filed on Oct. 23, 2020, 3 pages.
Teixeira et al., "Whey protein increases muscle weight gain through inhibition of oxidative effects induced by resistance exercise in rats", Nutrition Research, 2016, vol. 36, No. 10, pp. 1081-1089.
Kim et al., "Effects of Exercise and Amino Acid Supplementation on Body Composition and Physical Function in Community-Dwelling Elderly Japanese Sarcopenic Women: A Randomized Controlled Trial", Journal of the American Geriatrics Society, 2012, vol. 60, No. 1, pp. 16-23.

* cited by examiner

*Primary Examiner* — Christina Bradley
(74) *Attorney, Agent, or Firm* — Oblon, McClelland, Maier & Neustadt, L.L.P.

(57) ABSTRACT

Agents containing γ-glutamyl peptide can prevent a decline in muscle quality and improve muscle quality even when exercise is limited, and further, can effectively enhance the effect of exercise even when the exercise is of a level free of undue efforts.

9 Claims, 6 Drawing Sheets

[Fig. 5]
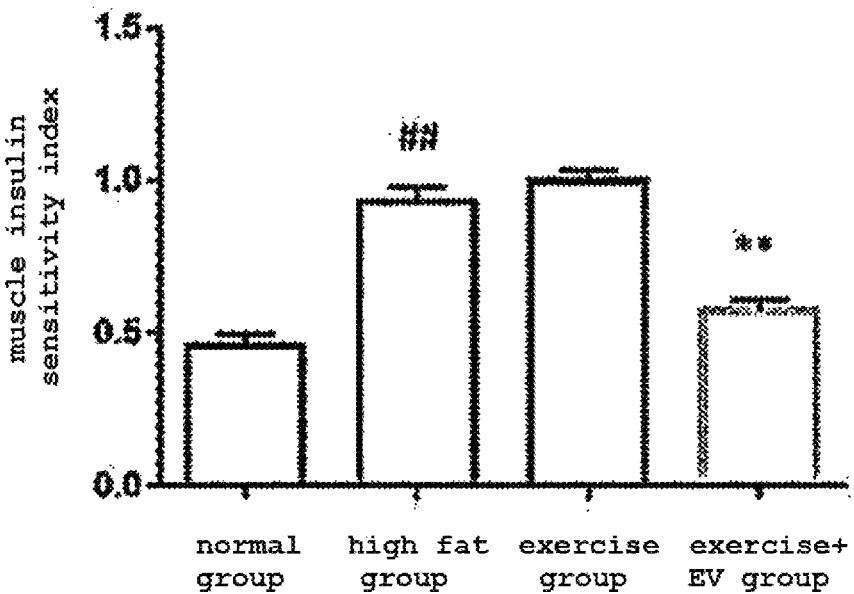
[Fig. 6]
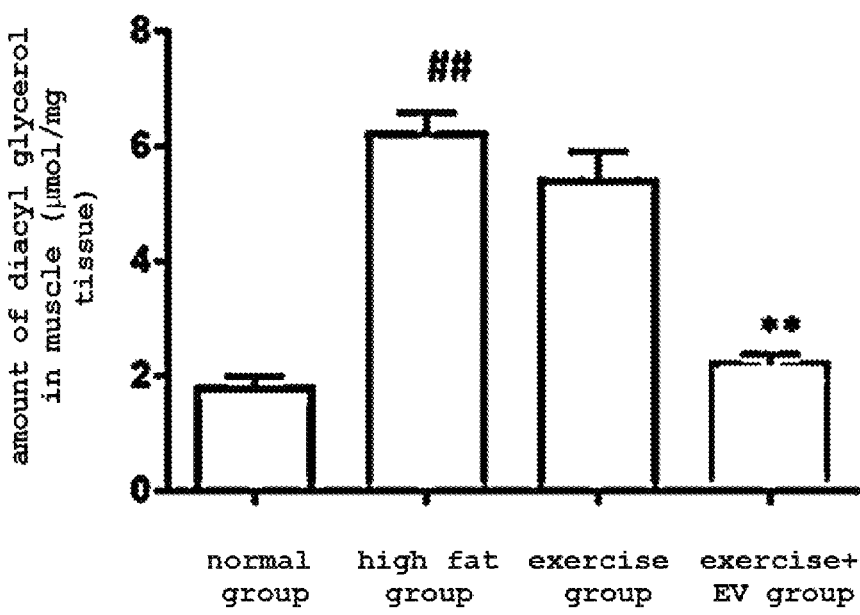

[Fig. 7]
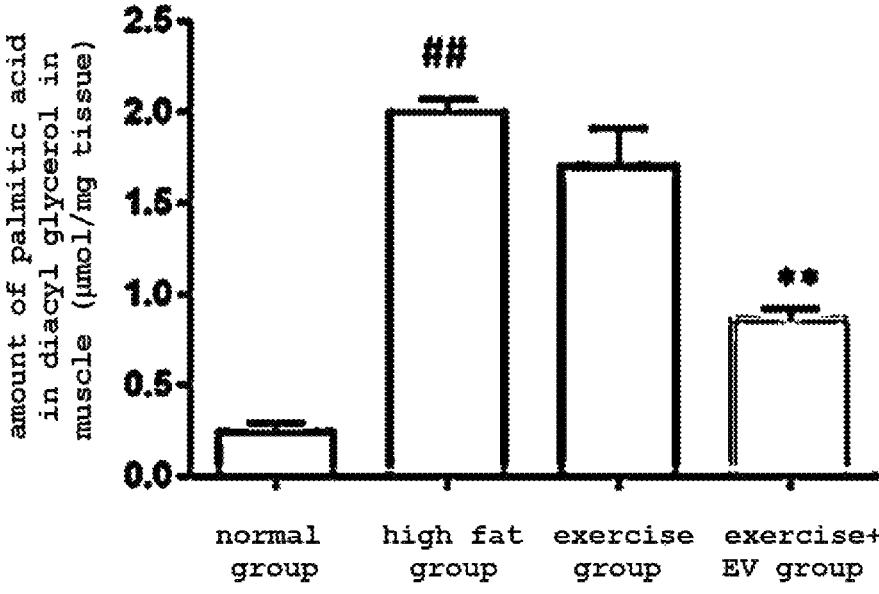
[Fig. 8]
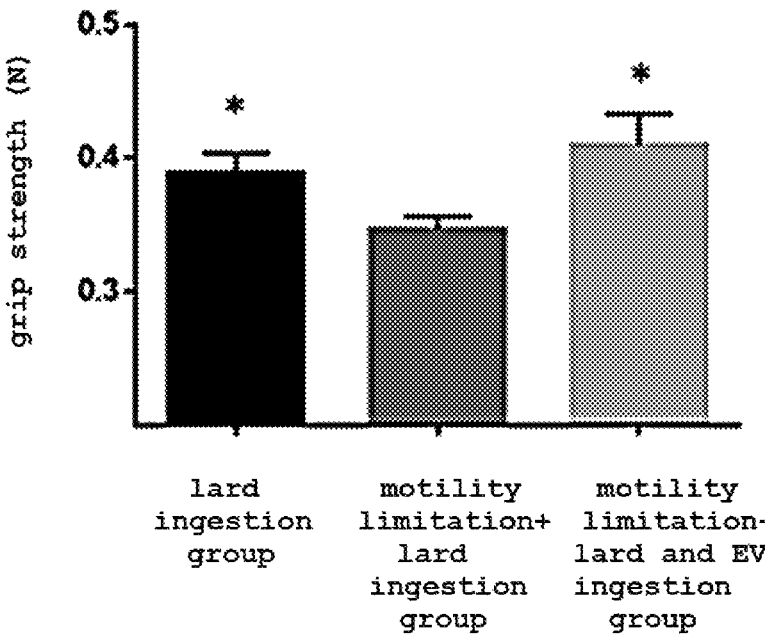

MUSCLE QUALITY IMPROVEMENT AGENT

CROSS REFERENCES TO RELATED APPLICATIONS

This application is a continuation of International Patent Application No. PCT/JP2020/039904, filed on Oct. 23, 2020, and claims priority to Japanese Patent Application No. 2019-194725, filed on Oct. 25, 2019, both of which are incorporated herein by reference in their entireties.

BACKGROUND OF THE INVENTION

Field of the Invention

The present invention relates to muscle quality-improving agents that can prevent a decline in muscle quality and improve muscle quality.

Discussion of the Background

In recent years, with the aging of the population, health disorders accompanied by a decline in physical function such as metabolic syndrome, locomotive syndrome, and frailty (a state between a healthy state and a state requiring nursing care) have become a social problem.

To deal with the situation, various efforts have conventionally been made mainly to increase skeletal muscle mass. For example, it has been reported that ingestion of essential amino acids including a high content of leucine is effective for muscle loss (sarcopenia) in old age (see H. K. Kim et al.; J. Am. Geriatr. Soc. 60 (1) 16-23 (2012), which is incorporated herein by reference in its entirety).

However, it has become clear that increasing skeletal muscle mass alone is not sufficient for restoring muscle strength.

In addition, it has become clear that a decline in the quality of muscle, that is, muscle quality, which was previously regarded as a change due to aging, is also caused by an unbalanced diet and lack of exercise, and leads to a serious condition such as locomotive syndrome, frailty, and the like in the future.

Exercise is known to be the most effective means of improving or preventing such decline in muscle quality. However, even if one desires to do exercise, it is often not possible to sufficiently perform exercise for various reasons such as decline in physical function due to aging, restriction on exercise due to illness, injury, etc., and the like.

Therefore, the development of a muscle quality-improving agent is desired that can prevent a decline in muscle quality, improve muscle quality, and effectively enhance the effect of exercise even when the exercise is one that can be performed without undue efforts.

SUMMARY OF THE INVENTION

Accordingly, it is one object of the present invention to provide muscle quality-improving agents that can prevent a decline in muscle quality and improve muscle quality even when exercise is limited, and further, can effectively enhance the effect of exercise even when the exercise is of a level free of undue efforts.

This and other objects, which will become apparent during the following detailed description, have been achieved by the present inventors' discovery that γ-glutamyl peptide has an effect of preventing a decline in muscle quality, or improving muscle quality.

Accordingly, the present invention provides the following.

(1) A muscle quality-improving agent comprising a γ-glutamyl peptide.

(2) The agent of (1), wherein the γ-glutamyl peptide is dipeptide or tripeptide.

(3) The agent of (1) or (2), wherein the γ-glutamyl peptide is one or more members selected from the group consisting of γ-glutamyl cysteine, γ-glutamyl valine, and γ-glutamyl valylglycine.

(4) The agent of any of (1) to (3), wherein the γ-glutamyl peptide is contained in 0.001 mM-100 mM.

(5) A medicament for improving muscle quality, comprising a muscle quality-improving agent of any of (1) to (4).

(6) A food for improving muscle quality, comprising a muscle quality-improving agent of any of (1) to (4).

(7) A method for improving the muscle quality of a target animal, comprising ingestion or administration of γ-glutamyl peptide in an amount effective for improving muscle quality of a target animal in need of improvement of the muscle quality.

(8) The method of (7), wherein the γ-glutamyl peptide is dipeptide or tripeptide.

(9) The method of (7) or (8), wherein the γ-glutamyl peptide is one or more selected from the group consisting of γ-glutamyl cysteine, γ-glutamyl valine, and γ-glutamyl valylglycine.

Advantageous Effects of Invention

The muscle quality-improving agent of the present invention can prevent a decline in muscle quality due to various reasons such as aging and the like and improve muscle quality even when exercise is limited, and further, can effectively enhance the effect of exercise even when the exercise is of a level free of undue efforts.

Therefore, it is useful for preventing a decline in muscle quality and improving muscle quality even in those having difficulty in performing the exercise conventionally considered necessary for improving muscle quality, which is caused by a decline in physical function due to aging, restriction of exercise due to illness, injury, etc., and the like.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 5 shows the evaluation results of the muscle insulin sensitivity index (IRS-1 serine phosphorylation activity) of each group in Experimental Example 2.

FIG. 6 shows the measurement results of the amount of diacyl glycerol in the muscle of each group in Experimental Example 2.

FIG. 7 shows the amount of palmitic acid in muscle diacyl glycerol of each group in Experimental Example 2.

FIG. 8 shows the measurement results of grip strength of each group in Experimental Example 3.

DETAILED DESCRIPTION OF THE PREFERRED EMBODIMENTS

Figure 1:
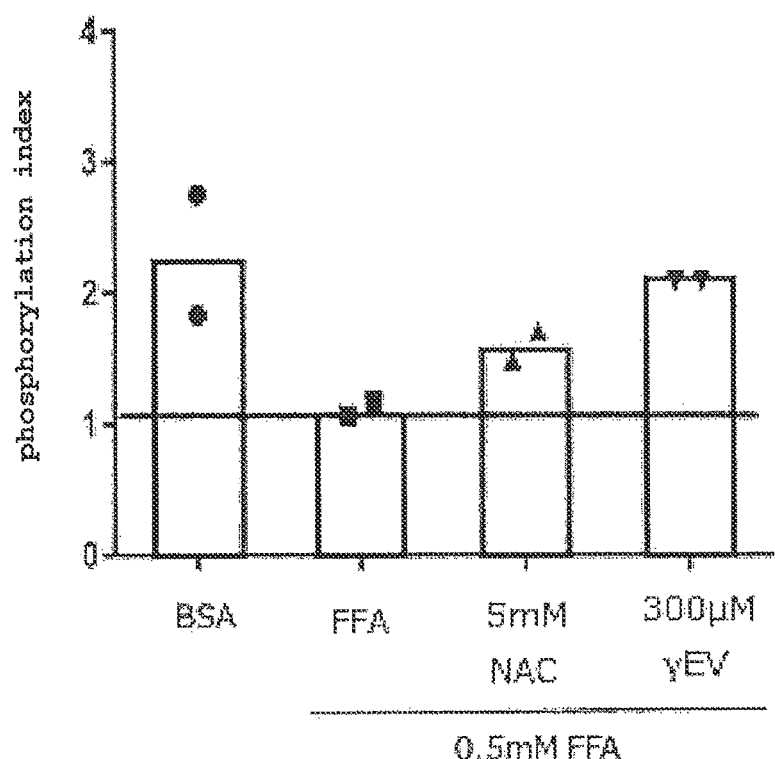
FIG. 1 shows the effects of γ-glutamyl valine on the decline in muscle insulin signal in Experimental Example 1.

The present invention provides a muscle quality-improving agent.

The muscle quality-improving agent of the present invention (hereinafter to be also referred to as the "agent of the present invention" in the present specification) contains γ-glutamyl peptide.

The "muscle quality" here refers to the quality of the muscle, or the condition of the muscle, as described above. Muscle is an aggregate of muscle fibers and tissues surrounding the muscle fibers, such as water, fat, connective tissue, and the like. In a muscle evaluated as having good muscle quality, the muscle fibers are dense and tissue surrounding the muscle fibers is less. When the number of muscle fibers decreases, or the muscle fibers become thinner, and the proportion of tissue other than muscle fibers increases, the muscle quality is evaluated to have declined. In addition thereto, other functions of muscle such as muscle mitochondrial function, muscle insulin sensitivity, muscle inflammation, lipid metabolism, protein synthesis, and the like are also elements of muscle quality. For example, along with deterioration of muscle, lipid metabolism function declines, fat accumulates easily, and muscle mitochondrial function and muscle protein synthesis function decline. The decline in these functions also leads to the evaluation of decline in muscle quality.

Therefore, "prevention of decline in muscle quality" refers to preventing muscle fibers from decreasing, muscle fibers from becoming thinner, or fat and connective tissue around muscle fibers from increasing, and maintaining muscle mitochondrial function, maintaining muscle insulin sensitivity, preventing muscle inflammation, or preventing decline in muscle lipid metabolism function and protein synthesis function. "Improvement of muscle quality" refers to increasing muscle fibers or making muscle fibers thick and dense, decreasing fat and connective tissue around muscle fibers, improving muscle inflammation and insulin sensitivity, and improving the intrinsic metabolic functions of muscles such as muscle mitochondrial function, lipid metabolism function, protein synthesis function, and the like to place muscles in good condition.

The "muscle quality-improving agent" in the present invention refers to one having the above-mentioned function to prevent decline in muscle quality, or one having the above-mentioned function to improve muscle quality, or one having the both functions.

The γ-glutamyl peptide contained in the agent of the present invention is a peptide compound having a γ-glutamyl group, that is, a peptide in which an amino group of amino acid binds to a carboxyl group at the γ-position of glutamic acid to form a peptide bond.

The glutamic acid and amino acid constituting the γ-glutamyl peptide to be used in the present invention may be any of D-form, L-form, and DL-form. From the aspect of muscle quality-improving effect, L-form or DL-form is preferred, and L-form is more preferred.

The γ-glutamyl peptide to be used in the present invention is, for example, a dipeptide, tripeptide, tetrapeptide, pentapeptide, oligopeptide or the like. The peptide chain length thereof is not particularly limited as long as a muscle quality-improving effect is afforded. It is generally 2 to 50, preferably 2 to 10, more preferably 2 to 5, particularly preferably 2 to 3.

Examples of the γ-glutamyl peptide preferably used in the present invention include γ-glutamyl cysteine, γ-glutamyl valine, γ-glutamyl valylglycine and the like. From the aspect of muscle quality-improving effect, γ-glutamyl valine is particularly preferred.

In the present invention, the above-mentioned γ-glutamyl peptide can be used not only in a free form but also a salt form. Various γ-glutamyl peptides in the present specification each show a concept encompassing even a salt. The salt form is not particularly limited as long as it is a pharmacologically acceptable salt, and an acid addition salt, a salt with base and the like can be mentioned.

Specifically, salts with inorganic bases, salts with organic bases, salts with inorganic acids, salts with organic acids, salts with an amino acid and the like can be mentioned.

Examples of the salts with inorganic bases include salts with alkali metals such as lithium, sodium, potassium and the like, salts with alkaline earth metals such as magnesium, calcium and the like, ammonium salt and the like.

Examples of the salts with organic bases include salts with alkanolamine such as monoethanolamine, diethanolamine, triethanolamine and the like, salts with heterocyclic amine such as morpholine, piperidine and the like, and the like.

Examples of the salts with inorganic acids include salts with hydrohalic acid (hydrochloric acid, hydrobromic acid, hydroiodic acid, etc.), sulfuric acid, nitric acid, phosphoric acid and the like, and the like.

Examples of the salts with organic acids include salts with a monocarboxylic acid such as formic acid, acetic acid, propanoic acid and the like; salts with a saturated dicarboxylic acid such as oxalic acid, malonic acid, malic acid, succinic acid and the like; salts with an unsaturated dicarboxylic acid such as maleic acid, fumaric acid and the like; salts with a tricarboxylic acid such as citric acid and the like; salts with a keto acid such as α-ketoglutaric acid and the like, and the like.

Examples of the salts with amino acid include salts with an aliphatic amino acid such as alanine and the like; salts with an aromatic amino acid such as tyrosine and the like; salts with a basic amino acid such as arginine and the like; salts with an acidic amino acid such as aspartic acid, glutamic acid and the like; salts with an amino acid forming lactam such as pyroglutamic acid and the like; and the like.

The above-mentioned salts may each be a hydrate (hydrate salt), and examples of the hydrate include 1 hydrate to 6 hydrate and the like.

The agent of the present invention may contain one kind of the above-mentioned γ-glutamyl peptide singly, or two or more kinds thereof in combination.

For the purpose of the present invention, a γ-glutamyl peptide in a free form is preferably used.

In the present invention, γ-glutamyl peptide in a free form or in the form of a salt to be used may be extracted from animals, plants or the like, which are naturally present, and purified, or obtained by a chemical synthesis method, a fermentation method, an enzyme method or a gene recombinant method. Commercially available products provided by each company may also be utilized.

The content of the γ-glutamyl peptide in the agent of the present invention when the agent of the present invention is in a liquid form is preferably 0.001 mM to 100 mM, more preferably 0.01 mM to 10 mM, further preferably 0.05 mM to 3 mM.

When the agent of the present invention is not in a liquid form but in a solid form or a semi-solid form, the content of the γ-glutamyl peptide in the agent of the present invention is preferably 0.001 wt % to 100 wt %, more preferably 0.005 wt % to 100 wt %, further preferably 0.01 wt % to 100 wt %, more further preferably 0.1 wt % to 100 wt %. When the γ-glutamyl peptide is in the form of a salt, the amount is based on the free form of the γ-glutamyl peptide.

The agent of the present invention can also contain other nutritional components and anti-fatigue agent and the like. As the nutrition component and the like, a carbohydrate preparation such as glucose, dextran and the like, a fat emulsion such as purified soybean oil, purified egg-yolk lecithin and the like, a protein preparation such as casein, whey protein and the like, caffeine, vitamins, minerals, polyphenols and the like can be specifically mentioned.

The agent of the present invention can have a dosage form of an oral preparation such as tablet, coating tablet, chewable tablet, pill, (micro)capsule, granule, fine granule, powder, elixir, lemonade, syrup, suspension, emulsion, oral jelly or the like, an injectable preparation, for example, an injection such as solution, suspension, emulsion or the like, a solid injection to be used by dissolving or suspending when in use, a transfusion, a sustainable injection or the like, and the like.

The agent of the present invention in the above-mentioned dosage form can be prepared by a formulating means well known in the field of preparations, for example, the methods described in the Japanese Pharmacopoeia, seventeenth Edition, General Rules for preparation, [3] Monographs for Preparations, which is incorporated herein by reference in its entirety.

In this case, various pharmacologically acceptable additives for preparations can be blended as necessary. The additive can be appropriately selected according to the dosage form of the agent of the present invention. For example, excipient, binder, disintegrant, lubricant, coating agent, base, solvent, diluent, solubilizing agent, solubilizer, emulsifier, dispersing agent, suspending agent, stabilizer, thickener, soothing agent, isotonicity agent, pH adjuster, antioxidant, antiseptic, preservative, corrigent, flavoring agent, sweetening agent, flavor, colorant and the like can be mentioned.

Specifically, examples of the excipient include magnesium carbonate, titanium dioxide, saccharides (lactose, etc.), sugar alcohol (mannitol, etc.), casein and the like.

Examples of the binder include gelatin, starch, cellulose and a derivative thereof and the like.

Examples of the disintegrant include crospovidone, crystalline cellulose and the like.

Examples of the lubricant include talc, magnesium stearate and the like.

Examples of the coating agent include methylmethacrylate·butylmethacrylate·dimethylaminoethyl methacrylate copolymer, ethylacrylate·methylmethacrylate·trimethylammmonioethyl methacrylate chloride copolymer and the like.

Examples of the base include animal oil, vegetable oil, hydrocarbon oil (liquid paraffin, etc.), polyethylene glycol and the like.

Examples of the solvent include purified water, water for injection, monovalent alcohol (ethanol, etc.), polyhydric alcohol (glycerol, etc.) and the like.

Examples of the emulsifier or dispersing agent include sorbitan fatty acid ester, glycerine fatty acid ester, polyoxyethylene sorbitan fatty acid ester, sucrose fatty acid ester and the like.

Examples of the stabilizer include adipic acid, β-cyclodextrin and the like.

Examples of the thickener include water-soluble polymer (sodium polyacrylate, carboxyvinyl polymer, etc.), polysaccharides (sodium alginate, xanthan gum, tragacanth, etc.) and the like.

Examples of the soothing agent include ethyl aminobenzoate, chlorobutanol, propylene glycol, benzyl alcohol and the like.

Examples of the isotonicity agent include potassium chloride, sodium chloride, sorbitol, physiological saline and the like.

Examples of the pH adjuster include hydrochloric acid, sulfuric acid, acetic acid, citric acid, lactic acid, sodium hydroxide, potassium hydroxide and the like.

Examples of the antioxidant include dibutylhydroxytoluene (BHT), butylhydroxyanisole (BHA), α-tocopherol, erythorbic acid and the like.

Examples of the antiseptic or preservative include paraben (methylparaben, etc.), benzyl alcohol, sodium dehydroacetate, sorbic acid and the like.

Examples of the corrigent or flavoring agent include ascorbic acid, erythritol, sodium L-glutamate and the like.

Examples of the sweetening agent include aspartame, licorice extract, saccharin and the like.

Examples of the flavor include l-menthol, d-camphor, cineol and the like.

Examples of the colorant include tar pigment (red No. 2, blue No. 1, yellow No. 4, etc.), inorganic pigment (red iron oxide, yellow iron oxide, black iron oxide, etc.), natural dye (annatto dye, turmeric dye, β-carotene, etc.) and the like.

The ingestion amount or dose of the agent of the present invention is appropriately determined according to the condition of muscle quality or degree of decline in muscle quality, gender, age, and body weight of the subject to whom the agent of the present invention is applied (hereinafter to be referred to as the "application target" in the present specification), dosage form of the agent of the present invention, administration method and the like. When the application target is a human adult, the amount of γ-glutamyl peptide (when contained in a salt form, an amount converted to a free form) is generally 0.01 mg/kg body weight to 10 g/kg body weight, preferably 0.05 mg/kg body weight to 5 g/kg body weight, more preferably 0.1 mg/kg body weight to 1 g/kg body weight, per day.

The above-mentioned amount of ingestion or dose can be taken once or in two or more portions (e.g., 2 to 5 portions) per day.

The timing of ingestion or administration of the agent of the present invention is not particularly limited, and it may be ingested or administered before or after meal, or together with meal. When exercise is performed, it may be ingested or administered at any timing of before start of the exercise, during the exercise, after completion of the exercise or the like.

While the number of ingestions or administrations of the agent of the present invention is not particularly limited, it is at least once (once or twice or more) when the muscle quality needs to be improved.

When the number of ingestions or administrations of the agent of the present invention is 2 or more, while the ingestion or administration period (period from the first ingestion or administration to the last ingestion or administration) of the agent of the present invention is not particularly limited, it is generally 6 hr to 4 weeks. To exhibit the effect more, it is preferably 1 day to 2 weeks, more preferably 3 days to 1 week.

Since γ-glutamyl peptide contained in the agent of the present invention is a peptide composed of amino acids with rich food experience and highly safe, the agent of the present invention can be ingested or administered continuously. In particular, it is preferably ingested or administered for a long period of time (e.g., 2 weeks or more) to prevent a decline in muscle quality.

The agent of the present invention can be formulated as a unit package form. In the present specification, the "unit package form" means a form of one or more units with a particular amount (e.g., intake per one time, etc.) as one unit is/are packed in one container or package. For example, a unit package form with intake per one time as one unit is referred to as "unit package form for intake per one time". A container or package used for the unit package form can be appropriately selected according to the form and the like of the agent of the present invention. For example, paper container or bag, plastic container or bag, pouch, aluminum can, steel can, glass bottle, pet bottle, PTP (press through pack) package sheet and the like can be mentioned.

The application target of the agent of the present invention includes mammals (human, mouse, rat, hamster, rabbit, cat, dog, bovine, horse, donkey, swine, sheep, monkey, etc.) and birds (chicken, etc.) and the like. When the agent of the present invention is applied to an application target animal other than human (hereinafter to be also simply referred to as "target animal"), the ingestion amount or dose of the agent of the present invention can be appropriately set according to the kind, sex, body weight and the like of the target animal.

The agent of the present invention can prevent a decline in muscle quality due to various reasons such as aging and the like and can improve muscle quality even when exercise is limited, and further, can effectively enhance the effect of exercise even when the exercise is of a level free of undue efforts.

Therefore, the agent of the present invention is preferably used for preventing a decline in muscle quality or improving muscle quality in those having difficulty in performing the exercise conventionally considered necessary for improving muscle quality, such as elderly people experiencing a decline in physical function due to aging, those under restriction of exercise due to illness, injury, etc., and the like.

The agent of the present invention can be used as it is or added with the above-mentioned additives such as an excipient, solvent, diluent and the like to give a medicament for improving muscle quality (hereinafter to be also referred to as "the medicament of the present invention" in the present specification).

The content of γ-glutamyl peptide in the medicament of the present invention (when contained in a salt form, an amount converted to a free form) is generally 0.001 wt % to 100 wt %, preferably 0.005 wt % to 100 wt %, more preferably 0.01 wt % to 100 wt %, further preferably 0.1 wt % to 100 wt %.

The dose of the medicament of the present invention can be appropriately determined according to the condition and degree of decline in muscle quality of patients to whom the medicament of the present invention is administered, and the age, gender, body weight and the like of the patients. It can be determined such that the dose of γ-glutamyl peptide is the above-mentioned daily dose.

The medicament of the present invention can be produced by a means of formulation well known in the field of pharmaceutical preparation, such as the method described in the Japanese Pharmacopoeia, seventeenth Edition, General Rules for Preparation, [3] Monographs for Preparations, which is incorporated herein by reference in its entirety, and the like.

The medicament of the present invention can be suitably administered to elderly people, patients, persons in need of nursing care and the like who show a decline in muscle quality or are at a risk of a decline in muscle quality.

Furthermore, the agent of the present invention can be used by adding to various foods. The food to which the agent of the present invention is added is not particularly limited, and may be any as long as it is a food, dessert, or the like in the form generally served for meals. For example, the agent of the present invention is added to drinks, and a suitable flavor is added when desired, whereby a drink (e.g., beverage etc.) can be provided. More specifically, the agent of the present invention can be added to, for example, juice, milk, confectionery, jelly, yogurt, candy and the like.

The agent of the present invention may be added to a food in an amount to be ingested per day such that the ingestion amount of γ-glutamyl peptide is the above-mentioned daily ingestion amount.

The present invention also provides a food for improving muscle quality containing the agent of the present invention (hereinafter to be also referred to as "the food of the present invention").

The food of the present invention contains the agent of the present invention and, where necessary, food additives such as production agent, thickening stabilizer, gum base, emulsifier, preservation, antioxidant, gloss agent, pH adjuster, sweetener, bitter taste, acidulant, colorant, flavor and the like. Alternatively, the food of the present invention can be provided in various forms containing the agent of the present invention and food or food starting materials, for example, drinks such as juice, beverage water, teas and the like; milk products such as lactobacillus drinks, fermented milk, butter, cheese, yogurt, processing milk, defatted milk and the like; meat products such as ham, sausage, hamburg steak and the like; fish meat paste products such as boiled fish paste, tube-like fish sausage, satsuma-age and the like; egg products such as rolled Japanese-style omelette, egg tofu and the like; confectioneries such as cookie, jelly, chewing gum, candy, snack confectionery, frozen dessert and the like; bread; noodles; pickles; smoked product; dried fish; food boiled down in soy; salt-preserved product; soups; seasonings, and may be provided as bottled food, canned food, retort pouch food. In addition, forms such as powder, granule, sheet, capsule, tablet, jelly and the like can be provided.

The food of the present invention can be preferably ingested by elderly people, person in need of nursing care, patients and the like who are at a risk of a decline in muscle quality or requesting improvement of muscle quality.

In addition, the food of the present invention can be preferably ingested widely by middle-aged people who are not elderly people but desire to prevent a decline in muscle quality or improve muscle quality, and those who wish to improve their muscle quality, such as those who do not require nursing care but are under restriction in performing exercise due to illness, injury, and the like.

Therefore, the food of the present invention can also be provided as food with health claims such as food for specified health uses, food with nutrient function, food with functional claims and the like for preventing a decline in muscle quality or improving muscle quality, special purpose foods such as food for sick people, food for the elderly and the like, health supplement and the like.

Furthermore, the agent of the present invention can be used by adding to a high density liquid diet or food supplement.

The "high density liquid diet" is a comprehensive nutritional food (liquid diet) adjusted to about 1 kcal/mL, which is designed based on the daily nutritional requirement and with sufficient consideration of the qualitative composition of each nutrient so that remarkable excessive or insignificant nutrients will not occur even when only this is ingested for a long period of time.

The "food supplement" in the present invention refers to one ingested to aid nutrition other than one ingested as a food, and also includes nutritional supplement, supplement and the like. When the agent of the present invention is added to a food supplement, it can be prepared in a form such as tablet, capsule, powder, granule, suspension, chewable, syrup and the like by adding other nutrition components and additives when desired.

The above-mentioned food of the present invention can be processed and produced by adding a food additive as necessary to the agent of the present invention or adding the agent of the present invention to a food or food starting materials, and applying a general food production method.

The content of γ-glutamyl peptide in the food of the present invention can be appropriately determined according to the kind or form of the food, the level of the muscle quality improving effect expected by the ingestion of the food and the like. The content of γ-glutamyl peptide (an amount converted to a free form when contained in a salt form) is generally about 0.001 wt % to 100 wt %, preferably about 0.005 wt % to 100 wt %, more preferably about 0.01 wt % to 100 wt %, further preferably about 0.1 wt % to 100 wt %.

The daily ingestion amount of the food of the present invention can be set as an amount that can achieve ingestion of the aforementioned daily ingestion amount of γ-glutamyl peptide in the agent of the present invention.

The present invention also provides a commercial package containing the agent of the present invention and a written matter stating that the agent of the present invention can or should be used for improving muscle quality.

Furthermore, the present invention also provides a method for improving muscle quality of a target animal in need of improvement of the muscle quality (hereinafter to be also referred to as "the method of the present invention" in the present specification).

The method of the present invention comprises ingestion or administration of γ-glutamyl peptide in an amount effective for improving muscle quality of a target animal in need of improvement of the muscle quality.

As the target animal of the method of the present invention, human and mammals other than human such as mouse, rat, hamster, rabbit, cat, dog, bovine, horse, donkey, swine, sheep, monkey and the like, and birds such as chicken and the like can be mentioned.

In the case of human, the method of the present invention can be widely applied to a person showing a decline in muscle quality, and a person who desires prevention of a decline in muscle quality or improvement of muscle quality. Particularly, it may be preferably applied to patients and the like who cannot perform sufficient exercise, such as elderly people and persons in need of nursing care who are experiencing a decline in physical function, those under restriction of exercise due to illness, injury, etc., and the like.

The ingestion amount or dose of γ-glutamyl peptide in the method of the present invention is appropriately determined according to the kind, age, gender, body weight, condition and degree of a decline in muscle quality of the target animal, and the like. An amount similar to the above-mentioned ingestion amount or dose of the agent of the present invention for a human or a target animal other than human can be ingested or administered at the frequency and period mentioned above.

The ingestion or administration method of γ-glutamyl peptide in the method of the present invention includes oral ingestion, oral administration, enteral tube administration, administration by infusion and the like. Oral ingestion or oral administration is preferable since convenient ingestion is possible without the need to perform under the guidance and supervision of a doctor at a medical institution.

Other features of the invention will become apparent in the course of the following descriptions of exemplary embodiments which are given for illustration of the invention and are not intended to be limiting thereof.

EXAMPLES

Experimental Example 1. Evaluation of Action of γ-Glutamyl Peptide on Decline in Muscle Insulin Signal Muscle anabolic signal was monitored by insulin signal, and the action of γ-glutamyl peptide on the decline of insulin signal was evaluated. As the γ-glutamyl peptide, the actions of γ-L-glutamyl-L-valine (γEV), γ-L-glutamyl-L-cysteine (γEC), and γ-L-glutamyl-L-valylglycine (γEVG) were evaluated.

The evaluation was performed using an evaluation system in which exposure of the mouse-derived muscle cell line C2C12 to saturated fatty acid results in a decline in insulin signal, as described below.

(1) Differentiation Induction into C2C12 Myotube Cell (Myotubes)

Using mouse C3H skeletal muscle myoblast cell line (C2C12 cell) (DS Pharma Biomedical Co., Ltd.), the evaluation was performed.

Induction of differentiation into myotube cells (Myotubes) was performed using cells with myoblast passage number of 12 to 18. Myoblasts were seeded in a 12-well (diameter=3 cm) plate at $0.3 \times 10^5$ to $0.5 \times 10^5$ cells/well. After confirmation that the cell proliferation state reached 90% confluent, the medium was replaced with DMEM supplemented with 2 (w/v) % horse serum (HS) and 1 (w/v) % penicillin-streptomycin-glutamine (2 (w/v) % HS, 1 (w/v) % P/S, 1 (w/v) % Gln/DMEM), and differentiation into myotube cells (Myotubes) was induced. After confirmation of differentiation into myotube cells (Myotubes), a muscle insulin signal evaluation system was constructed, and the action of each of γEV, γEC, and γEVG was evaluated using the constructed evaluation system.

(2) Evaluation of Muscle Insulin Signal

The myotube cells (Myotubes) were cultured overnight (17 hr to 24 hr) at 37° C. in a 0.5 mM palmitic acid (FFA)/0.5 (w/v) % albumin (BSA)/DMEM culture medium in the presence of 5 (v/v) % carbon dioxide.

After culturing overnight, the cells were preincubated for about 2 hr in DMEM (BSA/FFA free), stimulated by incubation (15 min to 20 min) with 100 nM insulin, and the myotube cells were collected (each n=1 to 2). From the collected cells, proteins were extracted with RIPA (Radio-Immunoprecipitation Assay) buffer (Cell Signaling Technologies Inc.), adjusted to a final protein concentration of 0.5 mg/mL, and used as samples.

The expression levels of phosphorylated Akt (pAkt) (Ser473) (#9271S; Cell Signaling Technologies Inc.), and total Akt (#9272S; Cell Signaling Technologies Inc.) in the above-mentioned sample were quantified by the Western blotting (WB) method. The expression level of each protein was quantified using Western blot-chemiluminescent imaging system (Fusion FX) (Vilber-Lourmat Inc.).

Each γ-glutamyl peptide was added simultaneously with FFA, and the muscle quality-improving effect was examined with the recovery of the muscle insulin signal as an index. The final concentration of γEV was adjusted to 100 μM or 300 μM, and the final concentrations of γEC and γEVC were adjusted to 500 μM. As a positive control, an antioxidative active substance N-acetylcysteine (NAC) 5 mM was used.

(3) Evaluation Results

Figure 2:
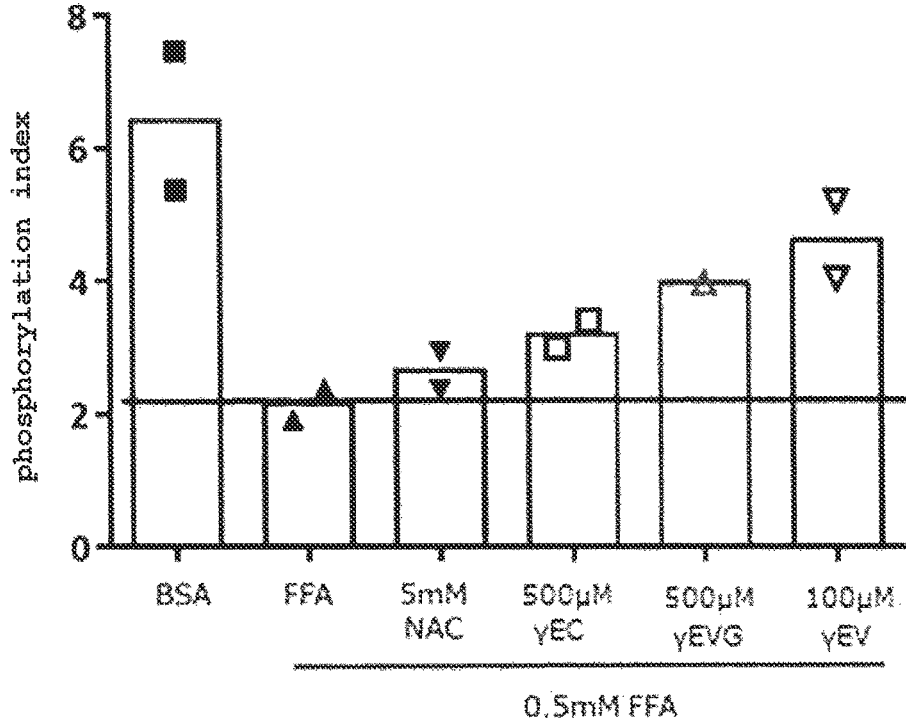
FIG. 2 shows the effects of various γ-glutamyl peptides on the decline in muscle insulin signal in Experimental Example 1.

From the measurement results of the expression levels of phosphorylated Akt (Ser473) and total Akt, the ratio of phosphorylated Akt and total Akt with insulin stimulation to the ratio of phosphorylated Akt and total Akt without insulin stimulation [(pAkt/Total Akt) Insulin+]/[(pAkt/Total Akt) Insulin-] was determined and shown in FIGS. 1 and 2 as the phosphorylation index (stimulation index). In the Figures, the average values of the calculated phosphorylation indices are shown in bar graphs. The symbols (●, ■, ▲, ▼, □, Δ, ∇) in the Figures indicate the calculated values of the phosphorylation index obtained for each sample.

As shown in FIG. 1, in myotube cells cultured with BSA added, an increase in the phosphorylation index was observed by stimulation with insulin, whereby it was shown that Akt phosphorylation was promoted. In myotube cells cultured with the addition of 0.5 mM FFA, phosphorylation of Akt due to insulin stimulation was suppressed, thus suggesting that FFA reduces muscle insulin signal.

On the other hand, it was confirmed that the decline in muscle insulin signal due to FFA was recovered by the addition of 300 μM γEV. In addition, γEV showed a muscle insulin signal increasing action equal to or higher than that of NAC at a concentration lower than that of NAC.

Furthermore, as shown in FIG. 2, γEV showed a muscle insulin signal increasing action superior to that of NAC even at a concentration of 100 μM.

In addition, it was found that γEC and γEVG also increase the insulin signal that declined due to FFA, like γEV.

From the results of the present Experimental Example, it was suggested that γ-glutamyl peptides such as γEV, γEC, γEVG and the like may be useful as a material that increases the muscle insulin signal.

Experimental Example 2. Evaluation of Action of γ-Glutamyl Peptide on Muscle Mass and Muscle Function (Exercise Function)

The action of γEV on muscle mass and muscle function (exercise function) were evaluated as follows.

The evaluation was performed using a model animal exhibiting a decline in muscle mass and a decline in muscle function due to the intake of a high-fat diet.

7-Week-old normal Sprague-Dawley (SD) male rats (CHARLES RIVER LABORATORIES JAPAN, INC.) were divided into 4 groups (n=6/group) as shown in Table 1, and supply of a normal feed (normal group) and a feed containing 30 wt % fat (high-fat diet) was started. γEV was supplied by adding same in an amount of 0.2 wt % to a diet containing 30 wt % fat.

Furthermore, the exercise groups (exercise group and exercise+γEV group) were made to perform exercise once a week under the exercise load conditions shown below.

At the 5th week of feeding the high-fat diet, the exercise function (walking function) was evaluated as follows. At the 6th week of feeding the high-fat diet, an autopsy was performed, and the muscle (tibialis anterior muscle) weight was measured. As described below, the muscle insulin sensitivity was evaluated, the fatty acid composition in muscle diacylglycerol was analyzed, and the muscle function was evaluated.

TABLE 1

| group | feed | exercise | number of n |
|---|---|---|---|
| normal group | 5 wt % fat-containing feed | No | 6 |
| high fat group | 30 wt % fat-containing feed | no | 6 |
| exercise group | 30 wt % fat-containing feed | Yes | 6 |
| exercise + EV group | 0.2 wt % γEV + 30 wt % fat-containing feed | yes | 6 |

(1) Exercise Load Conditions

The exercise was performed using the left leg of the rat by applying a local resistance exercise load. A rat under isoflurane anesthesia was placed in an ankle exercise device for small animals (Bioresearch Center K.K.), a skin stimulation electrode was attached to the tibialis anterior muscle, and contraction was caused by electrical stimulation. At the same time, the tibialis anterior muscle was pulled in the direction opposite to the contraction direction, and an extension load was applied. The exercise load setting conditions are shown below.

(i) contraction (electric) load condition: 4 mA to 5 mA, 100 Hz, 1100 msec (ii) extension load condition: angle of left leg joint was extended from 90° to 135° at rate=100 deg/sec (iii) exercise load frequency and number of times: 10 times per 10 seconds as 1 set, and 5 sets were repeated (total 50 times) with 60 sec recess between respective sets (2) Evaluation of Walking Function The walking function was evaluated by walking the rat without an anesthesia and observing the state of walking. India ink was applied to the plantar part of the both legs of the rat, and the rat was made to walk through a cylindrical tunnel with Japanese writing paper laid therein and the stride of walking (width and length) was measured based on the trace of the right leg and the left leg after walking, and the walking function was evaluated.

(3) Evaluation of Muscle Insulin Sensitivity

As an index of muscle insulin sensitivity, insulin receptor substrate-1 (IRS-1) serine phosphorylation activity was evaluated by a Western blotting (WB) method. Protein was extracted with RIPA (Radio-Immunoprecipitation Assay) buffer (Cell Signaling Technologies Inc.) from the muscle collected at the time of autopsy, adjusted to a final protein concentration of 2 mg/mL, and used as a sample.

As the antibodies, anti-Phospho-IRS-1 (Ser307) antibody (Cell Signaling Technologies Inc.), and anti-total IRS-1 antibody (Cell Signaling Technologies Inc.) were used, the expression levels of Phospho-IRS-1 (Ser307) and total IRS-1 were quantified using Western blot-chemiluminescent imaging system (Fusion FX) (Vilber-Lourmat Inc.).

As an index of insulin sensitivity, the ratio of Phospho-IRS-1 (Ser307) expression level to total IRS-1 expression level [(Phospho-IRS-1 (Ser307))/(total IRS-1)] was determined.

(4) Analysis of Fatty Acid Composition in Muscle Diacylglycerol

The amount of diacylglycerol (DAG) in muscle, which is highly related to muscle insulin sensitivity, was analyzed, and the composition of fatty acid contained in DAG was analyzed.

The fat ingredient in the muscle collected during autopsy was extracted according to a chloroform/methanol method, and the DAG fraction was extracted using thin layer chromatography (TLC). The DAG fraction was developed using a developer adjusted to heptane:acetic acid:diethyl ether=25:1:25 (volume ratio). DAG was quantified at 600 nm by a colorimetric method.

The DAG fraction after development was extracted by a chloroform/methanol method, and fatty acid in DAG was quantified. As fatty acids, 9 kinds of fatty acids (lauric acid, myristic acid, palmitoleic acid, palmitic acid, linolenic acid, linoleic acid, oleic acid, stearic acid, arachidonic acid) mainly contained in the living body were selected and analyzed using gas chromatography.

(5) Results

The respective measurement or evaluation or analysis results of the above-mentioned (2) to (4) are shown by mean±standard error in FIG. 3 to FIG. 7. The t-test was conducted between the normal group and the high fat group, and the Dunnett test was conducted between the high fat group and respective groups of the exercise group and the exercise+EV group, with respect to the respective measurement results and the like.

Figure 3:
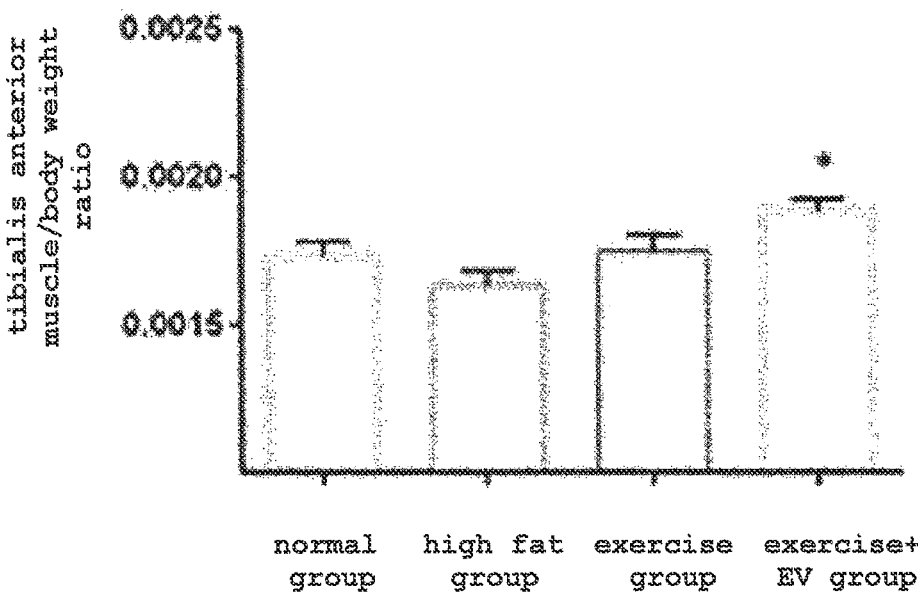
FIG. 3 shows the measurement results of the muscle (tibialis anterior muscle) weight of each group in Experimental Example 2.

(i) The measurement results of the muscle weight (weight of tibialis anterior muscle) are shown in a weight ratio to the body weight in FIG. 3. In the Figure, "*" means a significant difference from the high fat group at $p<0.05$.

The relative weight of the tibialis anterior muscle (exercise stimulation site) in the high fat group tended to decline as compared with the normal group. On the other hand, the muscle weight tended to increase by exercise, and increase in the muscle weight tended to be promoted in the group in which γEV was ingested in addition to performing exercise, as compared with the group in which only exercise was performed.

Figure 4:
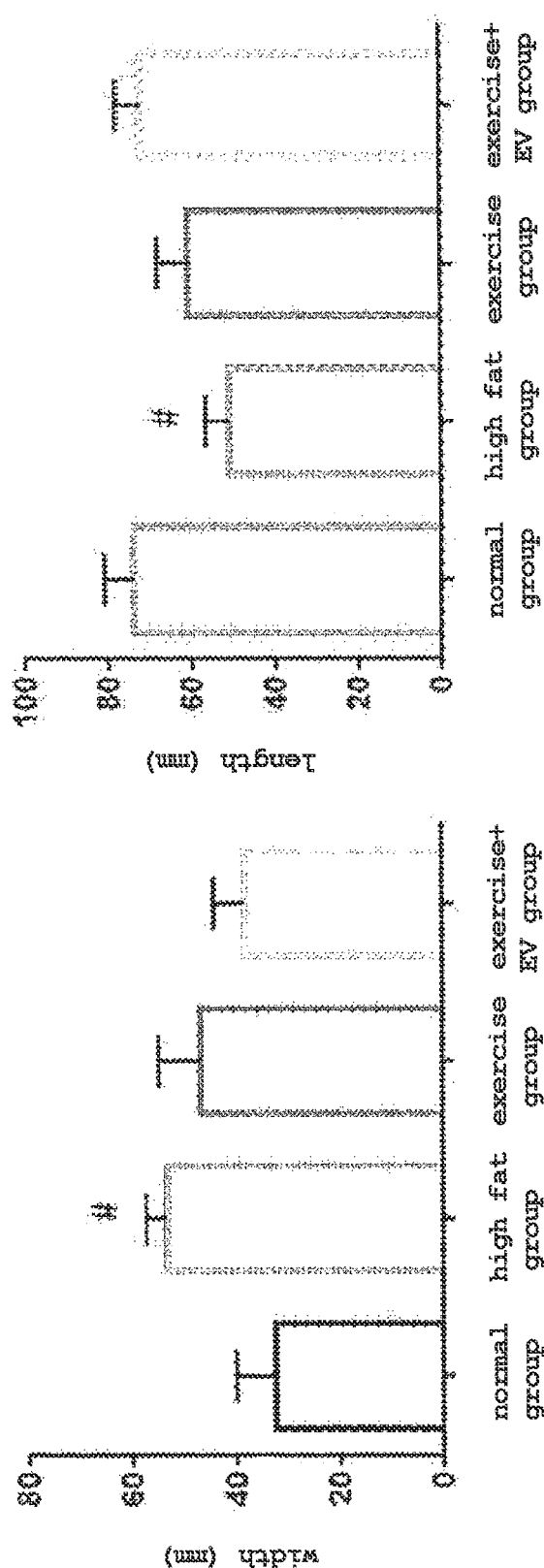
FIG. 4 shows the measurement results of the stride of walking (length and width) during walking of each group in Experimental Example 2.

(ii) The measurement results of the stride of walking (length and width) during walking are shown in FIG. 4. In the Figure, "#" means a significant difference from the normal group at $p<0.05$.

With respect to the stride of walking during walking in the high fat group, it was observed that the width was significantly wide as compared with the normal group, and the length was significantly narrow as compared with the normal group, and a decline in the walking function was suggested in the high fat group. It was found that the widening of the width and the narrowing of the length in the stride of walking observed after ingesting a high-fat diet tended to be suppressed by exercise. It was found that the aforementioned suppression tendency was enhanced by ingesting γEV in addition to exercise, and that in the exercise+EV group, they were suppressed to the same levels as in the normal group.

(iii) As an index of muscle insulin sensitivity, the evaluation results of the IRS-1 serine phosphorylation activity are shown in FIG. 5. In the Figure, "##" means a significant difference from the normal group at $p<0.01$, and "**" means a significant difference from the high fat group at $p<0.01$.

The ratio of Phospho-IRS-1 (Ser307) expression level to total IRS-1 expression level [(Phospho-IRS-1 (Ser307))/(total IRS-1)], which is an index of muscle insulin sensitivity, was significantly high in the high fat group as compared with the normal group, and a decline in the muscle insulin sensitivity was suggested. In the exercise group, the value of the muscle insulin sensitivity was of the same level as that of the high fat group, but a decline in the muscle insulin sensitivity was significantly suppressed by the ingestion of γEV in addition to exercise, and the value was found to be close to that of the normal group.

(iv) The measurement results of the amount of diacylglycerol (DAG) in skeletal muscle are shown in FIG. 6. In the Figure, "##" means a significant difference from the normal group at $p<0.01$, and "**" means a significant difference from the high fat group at $p<0.01$.

The amount of DAG in skeletal muscle, which DAG is considered to be involved in insulin sensitivity of skeletal muscle, was significantly increased in the high fat group as compared with the normal group. In the exercise+EV group, the increase in the amount of DAG was significantly suppressed, showing the same level of the amount of DAG as in the normal group. Thus, it was suggested that the accumulation of DAG due to the ingestion of high-fat diet is normalized by ingestion of γEV as well as performing exercise.

(v) As the analysis results of the composition of fatty acid in muscle diacylglycerol (DAG), the amount of palmitic acid in muscle DAG is shown in FIG. 7. In the Figure, "##" means a significant difference from the normal group at $p<0.01$, and "**" means a significant difference from the high fat group at $p<0.01$.

In the high fat group, the amount of saturated fatty acid (palmitic acid) in DAG was markedly higher, but in the exercise+EV group, it was significantly lower than in the high fat group. It was shown that the increase in the amount of palmitic acid due to the high-fat diet load is suppressed by exercise combined with ingestion of γEV.

From the results of this Experimental Example, it was suggested that there is a possibility that γ-glutamylpeptide further improves exercise function such as walking function by improving, in addition to recovery of muscle amount, muscle quality such as insulin sensitivity of muscle and lipid metabolism in muscle.

Experimental Example 3. Examination of Action of γ-Glutamyl Peptide on Muscle Quality and Muscle Function During Motility Limitation Using C57BL/6J mice, the effect of ingestion of γ-glutamyl peptide on the changes in muscle quality and muscle function induced by narrowing the area of the cage used for rearing to limit exercise was investigated.

C57BL/6J mice were grouped into 3 groups shown in Table 2 such that the body weight, grip strength, and lean body weight would be uniform, and one mouse was housed per cage and reared. As cages for rearing mice, a wide cage (width 220 mm×length 320 mm×height 165 mm) and a narrow cage (width 110 mm×length 160 mm×height 130 mm) were used. In addition, as an experimental diet, a diet containing 20 wt % casein and 7 wt % lard or a diet containing 20 wt % casein, 7 wt % lard, and 0.2 wt % γ-glutamyl valine (γEV) was supplied.

TABLE 2

| group | feed | number of n | cage |
|---|---|---|---|
| Lard ingestion group | 20 wt % casein + 7 wt % lard-containing feed | 6 | wide cage |
| motility limitation + lard ingestion group | 20 wt % casein + 7 wt % lard-containing feed | 6 | narrow cage |
| motility limitation + lard and EV ingestion group | 20 wt % casein + 7 wt % lard and 0.2 wt % γEV-containing feed | 6 | narrow cage |

(1) Evaluation of Muscle Strength

After rearing for 28 days under the above-mentioned conditions, the grip strength of each mouse was measured and the muscle strength was evaluated.

The grip strength of the mouse was measured using a grip strength meter for small animals ("Chatillon", Columbus Instruments). The mouse was allowed to grasp with fore-limbs an area ⅓ from the end of the handle of the small animal grip strength meter, the tail of the mouse was held and pulled slowly, and the numerical value when the mouse was judged to have failed to grasp the handle in the absence of resistance using the abdominal muscle of the mouse was adopted as the grip strength. The aforementioned grip strength was consecutively measured five times, and the average value was calculated and used as the grip strength value of each individual.

(2) Analysis of Amount of Neutral Fat in Muscle and Amount of Palmitic Acid in Neutral Fat in Muscle After the completion of the above-mentioned grip strength measurement, muscles (gastrocnemius muscles) were collected from the mice in each group, and the amount of neutral fat in the muscle, which is one of the indicators of muscle quality, and the amount of palmitic acid in neutral fat in the muscle were measured.

Fat ingredient was extracted according to a chloroform/methanol method from the collected muscle, and the neutral fat content was measured by a colorimetric method at 600 nm, as well as the neutral fat was fractionated and collected by thin layer chromatography (TLC). The neutral fat fraction was developed using a developer adjusted to heptane:acetic acid:diethyl ether=25:1:25 (volume ratio). The neutral fat fraction was extracted again by a chloroform/methanol method, and the composition of the fatty acid in the neutral fat was analyzed, and the amount of palmitic acid was measured. The composition of the fatty acid was analyzed by gas chromatography.

(3) Results

Figure 9:
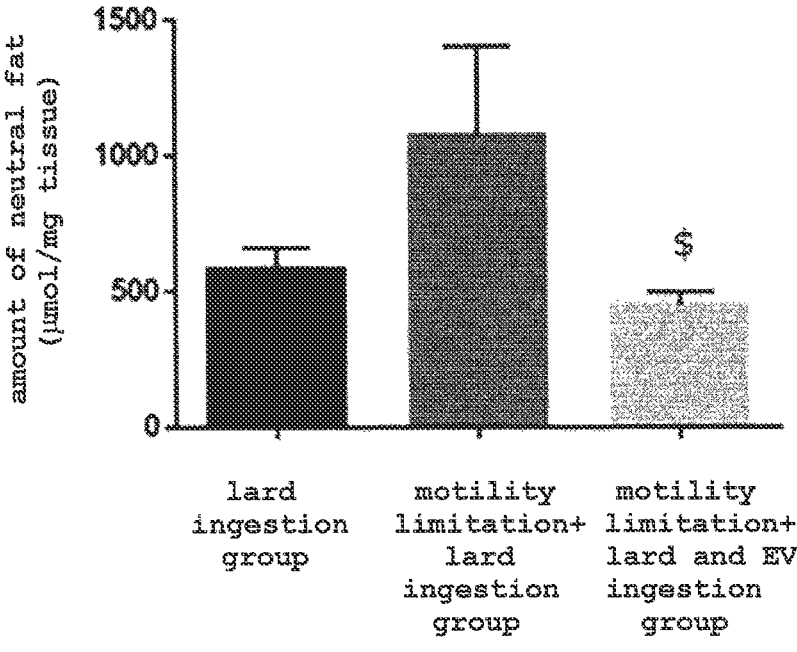
FIG. 9 shows the measurement results of the amount of neutral fat in the muscle of each group in Experimental Example 3.
Figure 10:
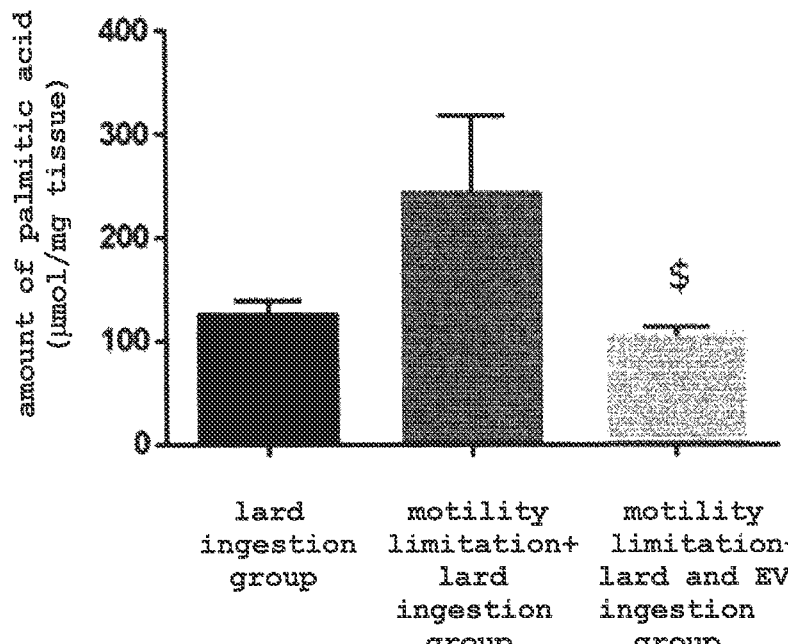
FIG. 10 shows the measurement results of the amount of palmitic acid in neutral fat in the muscle of each group in Experimental Example 3.

The measurement results of the grip strength in the above-mentioned (1) and the measurement results of the amount of neutral fat and the amount of palmitic acid in (2) are shown in FIGS. 8 to 10 each in mean±standard error.

In addition, a t-test was performed for each of the above-mentioned measurement results, between the motility limitation+lard ingestion group, and each of the lard ingestion group and the motility limitation+lard and EV ingestion group.

(i) FIG. 8 shows the measurement results of the grip strength of the mice in each group. In FIG. 8, "*" means a significant difference from the motility limitation+lard ingestion group at p<0.05.

As shown in FIG. 8, in the group reared in a narrow cage with motility limitation (motility limitation+lard ingestion group), the grip strength of the mice significantly (p<0.05) declined as compared with the group reared in a wide cage (lard ingestion group). On the other hand, in the group reared in a narrow cage with motility limitation and ingestion of γEV (motility limitation+lard and EV ingestion group), the grip strength of the mice was significantly (p<0.05) improved as compared with the motility limitation+lard ingestion group and found to be of the same level as the lard ingestion group free of limitation on exercise. Thus, it was shown that the ingestion of γEV suppressed the decline in grip strength due to the limitation on exercise.

(ii) FIG. 9 shows the measurement results of the amount of neutral fat in the muscle (gastrocnemius muscle) collected from the mice in each group. In FIG. 9, "$" means a significant difference from the motility limitation+lard ingestion group at p<0.1.

As shown in FIG. 9, it was found that the amount of neutral fat in the muscle increased in the motility limitation+lard ingestion group, as compared with the lard ingestion group. On the other hand, in the motility limitation+lard and EV ingestion group, the amount of neutral fat in the muscle was of the same level as that in the lard ingestion group, the amount of neutral fat in the muscle was significantly (p<0.1) small as compared with the motility limitation+lard ingestion group, an increase in the amount of neutral fat as seen in the motility limitation+lard ingestion group was not observed. Thus, it was shown that the ingestion of γEV suppressed accumulation of neutral fat in the muscle due to the limitation on exercise.

(iii) FIG. 10 shows the measurement results of the amount of palmitic acid in the neutral fat in the muscle (gastrocnemius muscle) collected from the mice in each group. In FIG. 10, "$" means a significant difference from the motility limitation+lard ingestion group at p<0.1.

The composition of fatty acid in the neutral fat accumulated in the muscle was investigated. As shown in FIG. 10, it was found that the amount of palmitic acid in neutral fat in the muscle, which is known as one of the factors causing decline in the muscle quality, increased in the motility limitation+lard ingestion group, as compared with the lard ingestion group. On the other hand, in the motility limitation+lard and EV ingestion group, the amount of palmitic acid was of the same level as that in the lard ingestion group, the amount of palmitic acid in the neutral fat in the muscle was significantly (p<0.1) small as compared with the motility limitation+lard ingestion group, an increase in the amount of palmitic acid as seen in the motility limitation+lard ingestion group was not observed. Thus, it was shown that the ingestion of γEV suppressed increase of palmitic acid in neutral fat in the muscle due to the limitation on exercise.

The results of this Experimental Example suggest that γ-glutamyl peptide suppresses decline in the muscle strength and suppresses decline in the muscle quality, even when exercise is limited.

INDUSTRIAL APPLICABILITY

As described in detail above, the present invention can provide a muscle quality-improving agent that can prevent a decline in muscle quality due to various reasons such as aging and the like and improve muscle quality even when exercise is limited, and further, can effectively enhance the effect of exercise even when the exercise is of a level free of undue efforts.

The muscle quality-improving agent of the present invention may be effectively used for preventing a decline in muscle quality and improving muscle quality even in those having difficulty in performing the exercise conventionally considered necessary for improving muscle quality, such as those under restriction of exercise caused by a decline in physical function due to aging, illness, injury, and the like.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A method for improving muscle quality, comprising administering to a subject in need thereof an effective amount of a γ-glutamyl peptide,
wherein said γ-glutamyl peptide is γ-glutamyl valine.

2. The method according to claim 1, wherein said γ-glutamyl peptide is administered in an amount of 0.01 mg/kg body weight to 10 g/kg body weight per day.

3. The method according to claim 1, wherein said γ-glutamyl peptide is administered in an amount of 0.05 mg/kg body weight to 5 g/kg body weight per day.

4. The method according to claim 1, wherein said γ-glutamyl peptide is administered in an amount of 0.1 mg/kg body weight to 1 g/kg body weight per day.

5. The method according to claim 1, wherein said subject is human.

6. The method according to claim 1, wherein said subject is an elderly person in need of nursing care.

7. The method according to claim 1, wherein said subject is experiencing a decline in physical function.

8. The method according to claim 1, wherein said subject is under restriction of exercise due to illness or injury.

9. The method according to claim 1, wherein the γ-glutamyl peptide is administered in the form of a composition which comprises said γ-glutamyl peptide in a concentration of 0.001 mM to 100 mM.

* * * * *